United States Patent [19]
Wolf et al.

[11] Patent Number: 5,756,819
[45] Date of Patent: May 26, 1998

[54] POLYAMINES CONTAINING TERT-BUTYL (METH) ACRYLATE GROUPS

[75] Inventors: Elmar Wolf, Rechlinghausen; Bernhard Schleimer, Marl, both of Germany

[73] Assignee: Huels Aktiengesellschaft, Marl, Germany

[21] Appl. No.: 584,485

[22] Filed: Jan. 11, 1996

[30]    Foreign Application Priority Data

Jan. 10, 1995 [DE] Germany ............ 195 00 427.2

[51] Int. Cl.[6] ............ C07C 229/26; C07C 229/28
[52] U.S. Cl. ............ 560/125; 560/169
[58] Field of Search ............ 560/125, 169

[56]    References Cited

FOREIGN PATENT DOCUMENTS 3934428  4/1991  Germany .

Primary Examiner—Bernard Dentz

Attorney, Agent, or Firm—Oblon, Spivak, McClelland, Maier & Neustadt, P.C.

[57]    ABSTRACT

Polyamines containing tert-butyl (meth)acrylate groups and having the general formula I

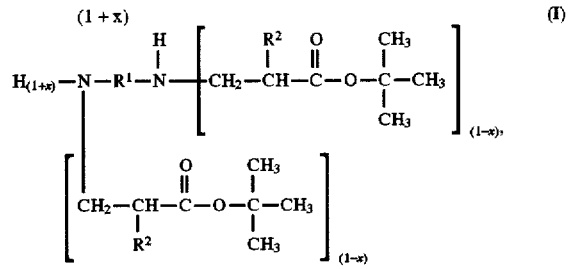

wherein $R^1$ represents a (cyclo)alkylene radical having 2–14 carbon atoms, which may optionally be substituted by 1–3 $CH_3$ or $C_2H_5$ groups and 1–3 $CH_2$ groups may be substituted by oxygen or —NH—, —NCH$_3$— or —C(O)NH— groups, $R^2$ denotes hydrogen or methyl and x may be a number between 1 and 0 with the proviso that $2(1-x) \geq 0.1$, are effective epoxy curing agents.

6 Claims, No Drawings

POLYAMINES CONTAINING TERT-BUTYL (METH) ACRYLATE GROUPS

BACKGROUND OF THE INVENTION

1. Field of the Invention

The present invention relates to polyamines containing tert-butyl (meth)acrylate groups and a process for their preparation.

2. Discussion of the Background

The polyamines used for curing epoxy resins are predominantly (cyclo)aliphatic polyamines. The epoxy resins cured with these polyamines are distinguished in practice by a number of desired properties, such as, for example, good adhesion to all possible substrates, good solvent resistance and high resistance to the effect of chemicals. In some cases, it has proved advantageous if cyanoethylated polyamines are used for curing epoxy resins. Thus, DE-AS 10 34 856 describes curable materials which have improved impact strength (in the cured state) and consist of a glycidyl polyether and a curing agent which was obtained by reacting an aliphatic polyamine with acrylonitrile.

DE-PS 21 64 099 describes cyanoethylated aliphatic polyamines, specifically diamines, which, as a mixture with epoxy compounds which contain more than one equivalent of epoxide groups per mol, in particular in solvent-free mixtures, have a relatively long pot life and cure with a non-tacky surface.

DE-OS 24 60 305 claims acrylonitrile adducts of cycloaliphatic diamines, which adducts in combination with liquid epoxy resins give low-stress moldings having little shrinkage and little susceptibility to cracking.

U.S. Pat. No. 3,478,081 mentions, as curing agents for epoxy resins, cyanoethylated bis(aminoalkyl) cyclohexanes which lead to moldings having good flexibility and high heat resistance.

A major disadvantage of these cyanoethylated polyamines lies in the handling of the carcinogenic acrylonitrile during the preparation of the acrylonitrile/ polyamine adducts. Simple substitution of the acrylonitrile by the noncarcinogenic acrylate in addition with polyamines is not possible because the adducts of acrylates and polyamines are not storage-stable. Slow amidation of the ester groups occurs at as low as room temperature.

SUMMARY OF THE INVENTION

It has now surprisingly been found that polyamines containing ester groups are storage-stable if they contain tert-butyl (meth)acrylate groups.

DETAILED DESCRIPTION OF THE PREFERRED EMBODIMENTS

The present invention thus relates to polyamines containing tert-butyl (meth)acrylate groups and having the formula I

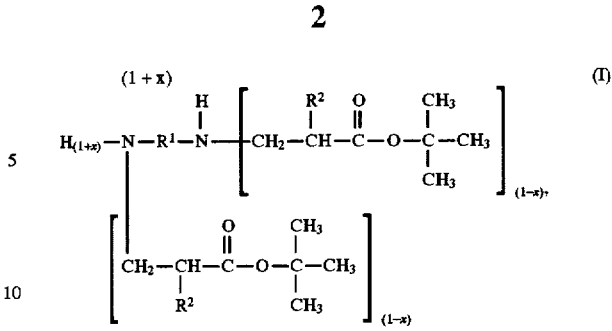

where $R^1$ represents a (cyclo)alkylene group having 2–14 carbon atoms, which may optionally be substituted by 1–3 $CH_3$ or $C_2H_5$ groups and 1–3 $CH_2$ groups may be substituted by oxygen, —NH—, —NCH$_3$— or —C(O)NH— groups, $R^2$ denotes hydrogen or methyl and x is a number between 1 and 0, with the proviso that $2(1-x) \geq 0.1$.

The term "(cyclo)alkylene" means alkylene, cycloalkylene or a mixture thereof. One or more carbon atoms on the (cyclo)alkylene group may be substituted with the described methyl or ethyl groups and/or 1–3 methylene groups of the (cyclo)alkylene group may be substituted by one of the groups noted above. The term "(meth)acrylate" means acrylate, methacrylate or a mixture thereof.

Preferred polyamines are those where $R^1$ denotes

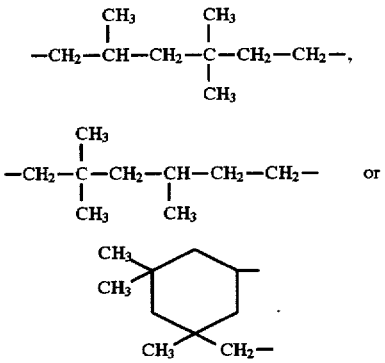

The compounds according to the invention are preferably characterized by a tert-butyl (meth)acrylate content of 0.1–2 mol (per mole of polyamine) and a basic amine content of 3–9 mmol $NH_2$/g. Their viscosity at room temperature (20°–25° C.) is about 100–10,000 mPa·s.

The present invention furthermore relates to a process for the preparation of the compounds according to the invention, characterized in that polyamines are reacted with tert-butyl (meth)acrylate according to the following equation.

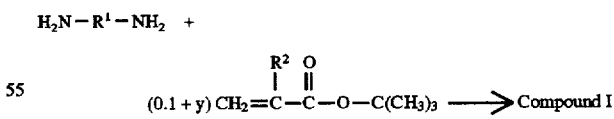

where $R^1$, $R^2$ have the above-mentioned meaning and y=0–1.9.

The polyamines to be used for the purposes of the present invention are (cyclo)aliphatic polyamines, such as, for example, 1,4-diaminobutane, neopentanediamine, 2-methylpentamethylenediamine, 5-methylnonamethylenediamine, 4,7-dioxadecane-1,10-diamine, 4,9-dioxadodecane-1,12-diamine, 4,7,10-trioxatridecane-1,13-diamine, 2,2,4(2,4,4)trimethylhexamethylenediamine (TMD), nonadecanediamine, bis(3-aminopropyl)methylamine, bis-hexamethylenetriamine, 4,4'-diaminodicyclohexylmethane, 3,3'-dimethyl-4,4'-diaminodicyclohexylmethane, 2,2-bis(4-aminocyclohexyl)propane, isophronediamine (IPD), 1,2-diaminocyclohexane and m-xylylenediamine.

In the process according to the invention, the tert-butyl (meth)acrylate in metered with thorough stirring into the polyamine heated to about 20°–80° C. in a polyamine to (meth)acrylate molar ratio of 1:(1+x), in such a way that the temperature of the reaction mixture does not exceed about 90° C. After the end of the addition of the tert-butyl (meth)acrylate, the reaction mixture is preferably further heated for about 1 hour at about 80° C. to complete the reaction. The compounds thus prepared contain, in principle for all values of y with the exception of y=1.9, unconverted polyamine and mono- and disubstituted polyamine. As a rule, the compounds according to the invention are further processed without further treatment, i.e. purification.

In some cases, it has proven expedient to prepare the compounds substantially free of the starting polyamine ($H_2N$—R—$NH_2$). In this case, the procedure adopted is one in which the polyamine is reacted with tert-butyl (meth) acrylate in a molar ratio of (5–10):1 and the unconverted polyamine is separated off from the reaction product after the end of the reaction by thin-film distillation at about 80°–170° C. and at about 0.1 to 0.01 mbar. The polyamine thus prepared contains only small amounts of unconverted polyamine. The concentration of N,N'-disubstituted polyamine depends on the molar ratio of the reactants. The greater the excess of polyamines, the lower is the concentration of disubstituted polyamine.

The compounds according to the invention are very suitable for curing epoxy resins whose processing requires extremely long pot lives. They are very particularly suitable for the preparation of aqueous 2-component epoxy systems.

Suitable epoxy resins and aqueous 2-component epoxy systems are well known in the art. The epoxy systems described in DE-AS 10 34 856, DE-PS 21 64 099, DE-OS 24 60 305 and U.S. Pat. No. 3,478,081 may be cured with the tert-butyl (meth)acrylate group-containing polyamine curing agents of the present invention. These references and the priority document, German patent application No. 195 00 427.2 filed Jan. 10, 1995, are incorporated herein by reference in their entirety.

Other features of the invention will become apparent in the course of the following descriptions of exemplary embodiments which are given for illustration of the invention, but are not intended to be limiting thereof.

EXAMPLES

Example 1

In a 1.0 liter three-necked flask, 256 parts by weight of tert-butyl acrylate were metered into 316 parts by weight of TMD at 60° C. with thorough stirring and blanketing with $N_2$, in such a way that the temperature of the reaction mixture did not exceed 90° C. After the end of the addition of the tert-butyl acrylate, the reaction temperature was further heated for about 1 hour at 80° C. The reaction product was composed of 20 mol % of TMD and distributed TMD (1 TMD+2 mol of tert-butyl acrylate) and 60 mol % of monosubstituted TMD (1 TMD+1 mol of tert-butyl acrylate).

The amine content of the reaction product did not change during storage (at room temperature and 50° C.).

| Amine content mmol of $NH_2$/g | = 6.91 |
|---|---|
| NH-active equivalent weight | = 95 |
| Viscosity (25° C.) mPa · s | = 90 |

Example 2

340 parts by weight of IPD were reacted with 256 parts by weight of tert-butyl acrylate in a manner analogous to Example 1.

| Amine content mmol of $NH_2$/g | = 6.70 |
|---|---|
| NH-active equivalent weight | = 99 |
| Viscosity (25° C.) mPa · s | = 370 |

The amine content of the reaction product did not change during storage (at room temperature and 50° C.).

Example 3

232 parts by weight of 2-methylpentamethylenediamine (DYTEK A) were reacted with 256 parts by weight of tert-butyl acrylate under the reaction conditions described in Example 2.

| Amine content mmol of $NH_2$/g | = 8.12 |
|---|---|
| NH-active equivalent weight | = 81 |
| Viscosity (25° C.) mPa · s | = 70 |

Example 4

340 by weight of IPD were reacted with 512 parts by weight of tert-butyl acrylate under the reaction conditions described in Example 1.

| Amine content mmol of $NH_2$/g | = 4.65 |
|---|---|
| NH-active equivalent weight | = 213 |
| Viscosity (25° C.) mPa · s | = 930 |

Example 5

158 parts by weight of TMD were reacted with 128 parts by weight of tert-butyl acrylate under the reaction conditions described in Example 1. After the end of the reaction, the unconverted TMD was separated by thin-film distillation at 80° C./0.1 mbar from the reaction product, which consisted of 95 mol % of monosubstituted TMD and 5 mol % of disubstituted TMD.

| Amine content mmol of $NH_2$/g | = 6.83 |
|---|---|
| NH-active equivalent weight | = 99 |
| Viscosity (25° C.) mPa · s | = 105 |

Comparative Example I 158 parts by weight of TMD were reacted with 128 parts by weight of n-butyl acrylate under conditions analogous to those stated in Example 1. The reaction product was not storage-stable.

| Amine content mmol of NH$_2$/g | = 6.816 on the 1st day |
| --- | --- |
| | 6.23 after 28 days |
| | 5.86 after 42 days |
| | 5.05 after 70 days |

The viscosity also increased with decreasing amine content, i.e., with increasing amidation.

Comparative Example II 170 parts by weight of IPD were reacted with 86 parts by weight of methyl acrylate under conditions analogous to those stated in Example 1. The reaction product was not storage-stable.

| Amine content mmol of NH$_2$/g | = 7.43 on the 1st day |
| --- | --- |
| | 6.49 after 30 days |
| | 5.78 after 120 days |

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by letters patent of the United States is:

1. A polyamine containing tert-butyl(methyl)acrylate groups and having formula I

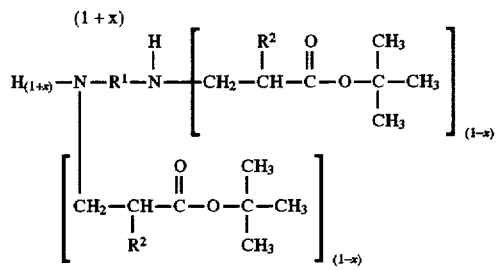

wherein $R^1$ is (cyclo)alkylene having 2-14 carbon atoms or said (cyclo)alkylene substituted by 1-3 $CH_3$ or $C_2H_5$ groups, where 1-3 $CH_2$ groups of said (cyclo)alkylene may be substituted by oxygen, —NH—, —NCH$_3$— or —C(O)NH— groups, $R^2$ is hydrogen or methyl, and x is a number between 1 and, but not including, 0, with the proviso that $2(1-x) \geq 0.1$, and with the additional proviso that either $R^2$ is methyl and/or $R^1$ contains nitrogen.

2. The polyamine of claim 1, wherein $R^1$ is

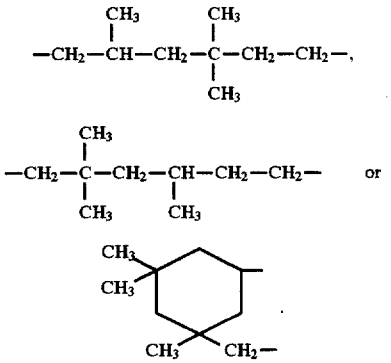

3. The polyamine of claim 1, having a tert-butyl (meth) acrylate content of 1-2 mol per mole of polyamine and a basic amine content of 3-9 mmol NH$_2$/g.

4. The polyamine of claim 1, having viscosity of about 100-10,000 mpa·s at 20°-25° C.

5. The polyamine of claim 1, wherein $R^2$ is methyl.

6. The polyamine of claim 1, wherein $R^1$ contains nitrogen.

* * * * *